United States Patent
Lim et al.

(10) Patent No.: US 9,802,064 B2
(45) Date of Patent: Oct. 31, 2017

(54) MICROCAPSULE COMPRISING GLYCOPROTEIN DERIVED FROM PLANTS

(71) Applicant: AMOREPACIFIC CORPORATION, Seoul (KR)

(72) Inventors: Hyung Jun Lim, Yongin-si (KR); Han Byul Kim, Yongin-si (KR); Do Hoon Kim, Yongin-si (KR); Song Seok Shin, Yongin-si (KR); Young Ho Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 97 days.

(21) Appl. No.: 14/431,566

(22) PCT Filed: Sep. 26, 2013

(86) PCT No.: PCT/KR2013/008632
§ 371 (c)(1),
(2) Date: Mar. 26, 2015

(87) PCT Pub. No.: WO2014/051353
PCT Pub. Date: Apr. 3, 2014

(65) Prior Publication Data
US 2015/0265503 A1  Sep. 24, 2015

(30) Foreign Application Priority Data

Sep. 28, 2012 (KR) .................. 10-2012-0109161
Sep. 13, 2013 (KR) .................. 10-2013-0110382

(51) Int. Cl.
| | |
|---|---|
| *A61K 8/02* | (2006.01) |
| *A61Q 19/00* | (2006.01) |
| *A61K 8/06* | (2006.01) |
| *A61K 8/64* | (2006.01) |
| *A61K 8/73* | (2006.01) |
| *A61K 8/11* | (2006.01) |

(52) U.S. Cl.
CPC ............. *A61Q 19/00* (2013.01); *A61K 8/11* (2013.01); *A61K 8/64* (2013.01); *A61K 8/645* (2013.01); *A61K 8/73* (2013.01); *A61K 2800/10* (2013.01); *A61K 2800/412* (2013.01); *A61K 2800/522* (2013.01)

(58) Field of Classification Search
CPC . A61K 8/645; A61K 8/73; A61K 8/64; A61K 8/11; A61K 2800/412; A61K 2800/10; A61K 2800/522; A61Q 19/00
See application file for complete search history.

(56) References Cited

U.S. PATENT DOCUMENTS

| | | | |
|---|---|---|---|
| 6,183,783 B1 * | 2/2001 | Benoit ................ | A61K 9/1694 424/401 |
| 2007/0141211 A1 * | 6/2007 | Kolar, Jr. .............. | A23D 9/06 426/302 |
| 2009/0061048 A1 * | 3/2009 | Kohane ................ | A23L 1/0029 514/1.1 |
| 2010/0303913 A1 * | 12/2010 | Gheith ................ | A61K 9/5169 424/488 |
| 2011/0117180 A1 | 5/2011 | Yan et al. | |
| 2012/0156288 A1 * | 6/2012 | Lakkis ................ | A23L 1/0029 424/455 |
| 2012/0164666 A1 | 6/2012 | Mullen | |

FOREIGN PATENT DOCUMENTS

| | | |
|---|---|---|
| KR | 1020040037016 A | 5/2004 |
| WO | 2004110413 A1 | 12/2004 |

OTHER PUBLICATIONS

Colon et al (Sep. 13, 2012). "Role of Catechins in the Antioxidant Capacity of an Active Film Containing Green Tea, Green Coffee, and Grapefruit Extracts." Journal of Agricultural and Food Chemistry, 60: 9842-9849.*
Benichou, et al., Double emulsions stabilized with hybrids of natural polymers for entrapment and slow release of active matters, Advances in Colloid and Interface Science, vol. 108-109 (2004) pp. 29-41.
International Search Report with English Translation for International Application No. PCT/KR2013/008632 dated Dec. 30, 2013.
Tong, et al., pH-responsive protein microcapsules fabricated via glutaraldehyde mediated covalent layer-by-layer assembly, OpenAccess Springer, Colloid Polym Sci (2008) vol. 286, No. 10, pp. 1103-1109.
Written Opinion for International Application No. PCT/KR2013/008632 dated Dec. 30, 2013.

* cited by examiner

*Primary Examiner* — Anoop Singh
*Assistant Examiner* — Doan Phan
(74) *Attorney, Agent, or Firm* — Cantor Colburn LLP

(57) ABSTRACT

The present invention relates to a microcapsule containing a glycoprotein derived from plants. Also, the present invention provides a microcapsule having oxidation ability and which is easy to prepare. Through said antioxidant capacity, oxidation and decomposition of an internally contained material can be prevented. According to the microcapsule of the present invention, the active components, in a form which was previously stabilized by a synthetic polymer derived from crude oil or by a surfactant, can be stabilized by naturally derived components. Also, since an organic solvent is not additionally used during the capsule preparation process, the preparation is simple and eco-friendly.

12 Claims, 15 Drawing Sheets

Example 8

Example 9

Example 10

Example 15

Example 17

Example 18

Example 20

Example 22

Example 24

Example 25

Example 26

Example 43

Example 44

Example 45

Example 48

Example 46

Example 49

Example 47

Example 50

MICROCAPSULE COMPRISING GLYCOPROTEIN DERIVED FROM PLANTS

TECHNICAL FIELD

The present disclosure relates to microcapsules including a plant-derived glycoprotein.

BACKGROUND ART

Novel stabilized capsules have been developed in order to develop a colloid stabilization system including a composite of edible biopolymer with protein. It is thought that when glycoproteins originated from plant peptides have anti-oxidative activity, it is possible to protect a material carried by capsules more stably. Particularly, many attempts have been made to accomplish such stabilization by introducing naturally occurring biopolymers as substitutes for conventional petroleum-derived synthetic polymers.

The present inventors have recognized that capsules including a plant glycoprotein in addition to a polysaccharide and protein can be prepared in a simple and convenient manner and have anti-oxidative activity, and thus significantly increase the stability of a material carried by such capsules. The present invention is based on this recognition.

DISCLOSURE

Technical Problem

The present disclosure is directed to providing microcapsules that have anti-oxidative activity and are prepared with ease.

Technical Solution

In one general aspect, there are provided microcapsules including: a polysaccharide having a negative net charge; a protein having an isoelectric point (PI) of 4-6; and a plant-derived glycoprotein having a negative net charge, and a method for preparing the same.

Advantageous Effects

The microcapsules according to the embodiments of the present invention have an advantage in that they can stabilize active ingredients of emulsion formulations, which, otherwise were stabilized by a plant-derived synthetic polymer or surfactant according to the related art, by using naturally occurring ingredients. In addition, since any organic solvent is not used separately during the preparation of such capsules, the preparation is more simple and eco-friendly. Additionally, the microcapsules according to the embodiments of the present invention facilitate the stabilization of effective ingredients in the form of soft microcapsules like hydrogels, not hard microcapsules, and allow the effective ingredients to realize their effects sufficiently. Further, the microcapsules according to the embodiments of the present invention are characterized in that they form or disintegrate stable particles reversibly depending on pH, and thus can be used as a pH-sensitive carrier. The microcapsules according to the embodiments of the present invention also have anti-oxidative activity, and thus can prevent the oxidation and decomposition of a material carried therein.

BEST MODE

Figure 1:
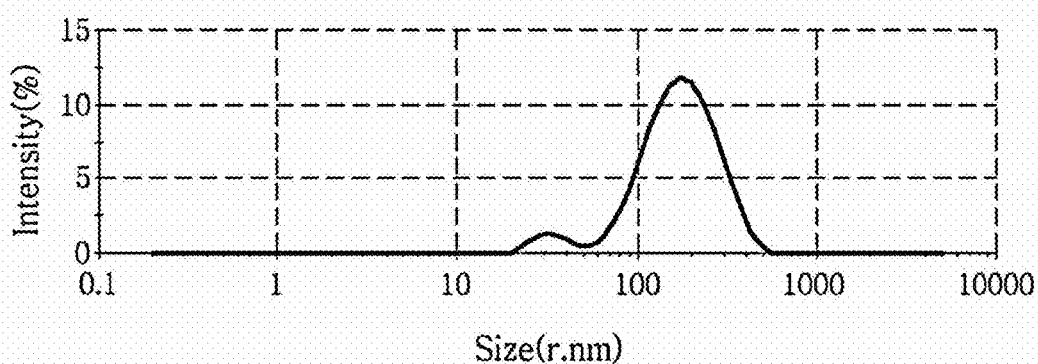
FIG. 1 is a graph showing the results of particle size analysis.

In one aspect, the present invention relates to microcapsules including: a polysaccharide having a negative net charge; a protein having an isoelectric point (PI) of 4-6; and a plant-derived glycoprotein having a negative net charge.

As used herein, the term 'polysaccharide' means a polysaccharide having a negative net charge in the presence of aqueous solution or water. Particularly, as used herein, the term 'polysaccharide' may have an anionic functional group, such as COOH, in its functional groups but is not limited thereto. Any polysaccharide may be used with no particular limitation, as long as the net charge obtained by adding all of the charges of polysaccharide functional groups is negative. More particularly, the polysaccharide may include, but is not limited to, pectin, xanthan, beet pectin, carrageenan, chitosan, gum arabic, inulin, methyl cellulose, xanthan gum, flaxseed gum, κ-carrageenan, ι-carrageenan, gellan gum, dextran sulfate, galactomannans, alginate or the like.

As used herein, the term 'protein' means a protein whose surface potential varies with a change in pH, i.e., a protein having an isoelectric point. Particularly, as used herein, the term 'protein' means a protein having an isoelectric point at pH 4-pH 6. Such proteins have a negative charge at pH 7 and may have a positive charge according to a change into an acidic condition. The protein disclosed herein may have a positive net charge at pH 4-pH 6 to form a complex with a polysaccharide and plant-derived glycoprotein, thereby forming microcapsules. The protein may be used as a surfactant. For example, the protein may include, but is not limited to, soy protein, casein, ovalbumin, lactoglobulin or the like.

As used herein, the protein may have an isoelectric point of at least 4, at least 4.2, at least 4.6, at least 4.8 or at least 4.9 and at most 6, at most 5.8, at most 5.6, at most 5.4, at most 5.2 or at most 5.1.

As used herein, the soy protein may include soybean protein but is not limited thereto. Any protein that can be obtained from beans may be used herein.

Particularly, the term 'soy' may be at least one selected from the group consisting of *Glycine max* (L.) Merr., *Phaseolus multiflorus* Willd. for. *albus* Bailey, *Canavalia lineata* (Thunberg) DC, *Cajanus Cajan* (L.) Millsp (pigeon pea), *Dipteryx odorata* (Aubl.) Willd, *Rhynchosia acuminatifolia* Makino, *Ceratonia siliqua* (L.) Taub., *Lablab purpureus* (L.) Sweet, *Vicia faba* L., *Cicer arietinum* L., *Rhyn-* chosai volubilis Loureira, *Rhynchosia nulubilis*, a seed of *Glycine soja* Sieb. et Zucc, *Lathyrus odoratus* Linne, *Amphicarpaea bracteata* subsp. *edgeworthii* (Benth.) H. Ohashi, *Vicia angustifolia* Linne var. *segetilis* (Thuill.) K. Koch., *Lathurus vaniotii* Leveille., *Dumasia truncata* Sieb. et Zucc., *Phaseolus muftiflous* Wild., *Lotus comiculatus* Linne var. *japonicus* Regel, *Dolichos lablab* L., *Amphicarpaea bracteata, Euchresta japonica* Hook fil. ex Regel., *Phaseolus lunatus* L., *Lens culinaris* Medik, *Arachis hypogaea* L., *Glycine max* Merrill, *Glycine soja* Sieb. et Zucc., *Canavalia gladiata* (Jacq.) DC., *Phaseolus vulgaris, Lupinus luteus, Phaseolus radiatus* L. var. *aurea, Glycine max* (L.) Merr., and *Phaseolus vulgaris* L.

As used herein, the soy protein or soybean protein may be isolated soy protein (ISP).

As used herein, the term 'plant-derived glycoprotein' also means a glycoprotein having a negative net charge in the presence of aqueous solution or water. As used herein, the plant-derived glycoprotein may have an anionic functional group such as COOH in the functional groups of sugar or protein but is not limited thereto. Any plant-derived glycoprotein may be used with no particular limitation, as long as the net charge obtained by adding all of the charges of functional groups is negative. Particularly, the plant-derived glycoprotein may include, but is not limited to, *bergenia* (*Bergenia cordifolia*)-derived glycoprotein, green tea-derived glycoprotein, *ginseng*-derived glycoprotein, pine tree leave-derived glycoprotein, *rhodiola*-derived glycoprotein and *abies* (*Abies Sibirica*)-derived glycoprotein or the like. In addition, the plant-derived glycoprotein also has anti-oxidative activity, and thus can prevent oxidation of a material carried by microcapsules.

The microcapsules according to the embodiments of the present invention may be prepared stably by complexing a protein having a positive charge in an acidic condition with a glycoprotein and polysaccharide having a negative charge. The microcapsules according to the embodiments of the present invention cause little irritation, because the glycoprotein, a naturally occurring plant-derived ingredient, functions as a surfactant. In addition, the microcapsules according to the embodiments of the present invention require no additional organic solvent for the preparation thereof, and thus are prepared with ease in an eco-friendly manner. Further, the microcapsules according to the embodiments of the present invention are characterized in that they form or disintegrate stable particles reversibly depending on pH, and thus can be used advantageously as a pH-sensitive carrier.

In the microcapsules according to the embodiments of the present invention, the plant-derived glycoprotein includes at least one selected from the group consisting of *bergenia*-derived glycoprotein, green tea-derived glycoprotein, *ginseng*-derived glycoprotein, pine tree leave-derived glycoprotein, *rhodiola*-derived glycoprotein and *abies*-derived glycoprotein. The glycoprotein has anti-oxidative activity to prevent oxidation and decomposition of a material carried by microcapsules, and is a naturally occurring material that causes little irritation.

In the microcapsules according to the embodiments of the present invention, the plant-derived glycoprotein may have a carboxylic acid functional group. The plant-derived glycoprotein may have a carboxylic acid functional group in its sugar or protein.

In the microcapsules according to the embodiments of the present invention, the polysaccharide includes at least one selected from the group consisting of pectin, xanthan, beet pectin, carrageenan, chitosan, gum arabic, inulin, methyl cellulose, xanthan gum, flaxseed gum, κ-carrageenan, ι-carrageenan, gellan gum, dextran sulfate, galactomannans, and alginate. Particularly, the pectin may be high methoxy pectin (HMP). High or low methoxy pectin is determined by how many carboxyl groups in the main chain are substituted with methyl ester groups. As used herein, HMP means pectin in which at least 50% of carboxyl groups are substituted with methyl ester groups. Particularly, such high methoxy pectin means pectin in which 69-74% of carboxyl groups are substituted with methyl ester groups.

In the microcapsules according to the embodiments of the present invention, the protein may be at least one selected from the group consisting of soy protein, casein, ovalbumin and lactoglobulin.

In the microcapsules according to the embodiments of the present invention, the weight ratio of polysaccharide:protein may be 1-9:1. When preparing microcapsules by using the above-defined weight ratio, it is possible to obtain a larger number of microcapsules having a more uniform particle size. In this context, the weight ratio of polysaccharide:protein may be 1-8:1, 1-7:1, 1-6:1, 1-5:1, 1-4:1, 1-3:1 or 1-2:1, particularly 1-2.3:1.

In the microcapsules according to the embodiments of the present invention, the weight ratio of polysaccharide:protein:glycoprotein may be 1-9:1:0.01-0.99. When preparing microcapsules by using the above-defined weight ratio, it is possible to obtain a larger number of microcapsules having a more uniform particle size and to maximize the anti-oxidative activity of microcapsules. In this context, the weight ratio of polysaccharide:protein:glycoprotein may be 1-7:1:0.01-0.9, 1-5:1:0.01-0.8 or 1-3:1:0.01-0.7.

In the microcapsules according to the embodiments of the present invention, the microcapsules may include a fat-soluble material inside their interfaces. The microcapsules according to the embodiments of the present invention have anti-oxidative activity, and thus can prevent oxidation and decomposition of the fat-soluble material carried in the microcapsules.

As used herein, the term 'fat-soluble material' includes a material that is immiscible with a water-soluble material and is present in a layer separated therefrom. The fat-soluble material may include a compound or extract soluble in fat. The fat-soluble material may include a material having an effective or active ingredient to provide a desired effect. When a fat-soluble active ingredient is carried in the microcapsules when preparing cosmetic, pharmaceutical or health-aid food products and producing, distributing and selling such products, it is possible to prevent oxidation and to cause little irritation by virtue of the presence of the plant-derived glycoprotein. Particularly, as used herein, the term 'fat-soluble material' includes any oil-soluble active ingredient that can be dissolved in ester-based oil, triglyceride-based oil, silicone-based oil or hydrocarbon-based oil with no particular limitation, and also covers effective ingredients that belong to terpenoids and flavonoids.

In the microcapsules according to the embodiments of the present invention, the fat-soluble material may be at least one selected from the group consisting of coenzyme Q10, carnosic acid, omega-3 and beta-carotene.

In another aspect, the present invention relates to a method for preparing microcapsules, including the steps of:
(a) mixing a fat-soluble material with water to form oil drops;
(b) allowing the oil drops to react with a polysaccharide having a negative net charge, a protein having an isoelectric point (PI) of 4-6, and a plant-derived glycoprotein having a negative net charge, at pH 4-pH 6.

In the method according to the embodiments of the present invention, steps (a) and (b) may be carried out at pH 6-pH 7.

The method according to the embodiments of the present invention may further include step (c) reducing pH of emulsion that has been subjected to secondary emulsification to pH 4-5.5, thereby forming microcapsules.

In the method according to the embodiments of the present invention, pH of step (c) may be pH 4.2-5.5, pH 4.4-5.5, pH 4.5-5.5, pH 4.6-5.4, pH 4.7-5.3, pH 4.8-5.2 or pH 4.9-5.1. Preferably, pH in step (c) may be approximately 5, particularly pH 4.8-5.2.

As used herein, the term 'water-soluble material' may include a material that cannot be miscible with and integrated into the fat-soluble material and is present in a layer separated from the fat-soluble material. Particularly, the water soluble material used herein may include water but is not limited thereto.

As used herein, the term 'oil drop' means a fat material present in the form of drops or droplets in the gaps of water-soluble material. The microcapsules according to the embodiments of the present invention include the oil drops enclosed with a protein as a surfactant, and thus make the internal environment of the oil drops more completely anhydrous. In addition to this, a highly viscous polysaccharide such as pectin is introduced to form bondings, thereby preventing incorporation of a water-soluble material more strongly.

In the method for preparing microcapsules according to the embodiments of the present invention, step (b) may include allowing the oil drops to react with the polysaccharide and plant-derived glycoprotein after the reaction with the protein. In the method, the oil drops react with the protein first to provide a more perfect anhydrous environment advantageously.

In the method for preparing microcapsules according to the embodiments of the present invention, the step of reaction with the polysaccharide and plant-derived glycoprotein may be carried out by allowing the plant-derived glycoprotein to react first, and then allowing the polysaccharide to react. When the plant-derived glycoprotein reacts first, it can exist more closely to the material carried by the microcapsules so that the anti-oxidative activity for the material may be maximized. In addition, in this case, since the polysaccharide having a negative net charge exists in the exterior of microcapsules and the microcapsules have the properties as particles having negatively charged surfaces, it is possible to prevent the coalescence of particles, thereby improving the stability of particles.

In the method for preparing microcapsules according to the embodiments of the present invention, the fat-soluble material in step (a) may include a mixture of a fat-soluble material with oil. As used herein, the oil may include silicone-based oil, hydrocarbon-based oil, triglyceride-based oil or ester-based oil, and any oil that can dissolve the fat-soluble material as an active ingredient at a high content may be used with no particular limitation. In the method for preparing microcapsules according to the embodiments of the present invention, the plant-derived glycoprotein includes at least one selected from the group consisting of *bergenia*-derived glycoprotein, green tea-derived glycoprotein, *ginseng*-derived glycoprotein, pine tree leave-derived glycoprotein, *rhodiola*-derived glycoprotein and *abies*-derived glycoprotein.

In the method for preparing microcapsules according to the embodiments of the present invention, the plant-derived glycoprotein may include a carboxylic acid functional group.

In the method for preparing microcapsules according to the embodiments of the present invention, the polysaccharide may include at least one selected from the group consisting of pectin, xanthan, beet pectin, carrageenan, chitosan, gum arabic, inulin, methyl cellulose, xanthan gum, flaxseed gum, κ-carrageenan, ι-carrageenan, gellan gum, dextran sulfate, galactomannans, and alginate.

In the method for preparing microcapsules according to the embodiments of the present invention, the protein may be at least one selected from the group consisting of soy protein, casein, ovalbumin and lactoglobulin.

In the method for preparing microcapsules according to the embodiments of the present invention, the weight ratio of polysaccharide:protein may be 1-9:1. When preparing microcapsules by using the above-defined weight ratio, it is possible to obtain a larger number of microcapsules having a more uniform particle size. In this context, the weight ratio of polysaccharide:protein may be 1-8:1, 1-7:1, 1-6:1, 1-5:1, 1-4:1, 1-3:1 or 1-2:1, particularly 1-2.3:1.

In the method for preparing microcapsules according to the embodiments of the present invention, the weight ratio of polysaccharide:protein:glycoprotein may be 1-9:1:0.01-0.99. When preparing microcapsules by using the above-defined weight ratio, it is possible to obtain a larger number of microcapsules having a more uniform particle size and to maximize the anti-oxidative activity of microcapsules. In this context, the weight ratio of polysaccharide:protein:glycoprotein may be 1-7:1:0.01-0.9, 1-5:1:0.01-0.8 or 1-3:1:0.01-0.7.

In still another aspect, the present invention relates to an emulsion composition including the microcapsules disclosed herein or microcapsules obtained by the method for preparing microcapsules disclosed herein.

In the emulsion composition according to the embodiments of the present invention, the protein may be present in an amount of 0.1-1 wt % based on the total weight of the finished composition including the microcapsules. More particularly, in the emulsion composition according to the embodiments of the present invention, the protein may be present in an amount of 0.01-5 wt %, 0.05-4.5 wt %, 0.1-4 wt %, 0.2-3.5 wt %, 0.3-3 wt %, 0.4-2.5 wt %, 0.5-2 wt %, 0.6-1.5 wt %, or 0.7-1 wt % based on the total weight of the finished composition including the microcapsules.

In the emulsion composition according to the embodiments of the present invention, the polysaccharide may be present in an amount of 1-3 wt % based on the total weight of the finished composition including the microcapsules. More particularly, in the emulsion composition according to the embodiments of the present invention, the polysaccharide may be present in an amount of 0.1-5 wt %, 0.5-4 wt %, 1-3.5 wt %, 1.3-3 wt %, 1.6-2.7 wt %, or 2-2.4 wt % based on the total weight of the finished composition including the microcapsules.

In the emulsion composition according to the embodiments of the present invention, the fat-soluble material may be present in an amount of 0.01-30 wt % based on the total weight of the finished composition including the microcapsules. More particularly, in the emulsion composition according to the embodiments of the present invention, the fat-soluble material may be present in an amount of 0.001-30 wt %, 1-25 wt %, 10-20 wt %, 12-18 wt %, or 14-16 wt % based on the total weight of the finished composition including the microcapsules.

In yet another aspect, the present invention relates to a method for preparing microcapsules, including the steps of:

i) emulsifying a fat-soluble material preliminarily with a protein having an isoelectric point (PI) of 4-6 to form preliminary o/w emulsion; and ii) secondary emulsifying formed preliminary emulsion with a polysaccharide having a negative net charge and a plant-derived glycoprotein having a negative net charge.

The method for preparing microcapsules according to the embodiments of the present invention may be carried out at room temperature.

In the method for preparing microcapsules according to the embodiments of the present invention, steps i) and ii) may be carried out under pH 6-7.

The method for preparing microcapsules according to the embodiments of the present invention may further include step iii) reducing pH of the secondary emulsified emulsion to pH 4-5.5, thereby forming microcapsules.

In the method for preparing microcapsules according to the embodiments of the present invention, pH in step iii) may be pH 4.2-5.5, pH 4.4-5.5, pH 4.5-5.5, pH 4.6-5.4, pH 4.7-5.3, pH 4.8-5.2 or pH 4.9-5.1. Preferably, pH in step iii) may be approximately 5, particularly pH 4.8-5.2.

Hereinafter, the present invention will be described more fully hereinafter with reference to Examples. The following Examples are for illustrative purposes only and it is apparent to those skilled in the art that the scope of the present invention is not limited by the Examples.

EXAMPLES

[Example I] Preparation of HMP/SC Capsules

The following experiment is carried out according to the following composition. The high-methoxy pectin used in this Example is Genu® Pection (CP Kelco, Denmark). This is pectin in which 69-74% of carboxyl groups are substituted with methyl ester groups. Sodium caseinate is commercially available from American Casein Company.

TABLE 1

|  | Unit (wt %) | | | |
| --- | --- | --- | --- | --- |
| Ingredients | Ex. 1 | Ex. 2 | Ex. 3 | Ex. 4 |
| Water | Balance | Balance | Balance | Balance |
| High Methoxy Pectin (HMP) 3% aqueous solution | 3 | | | |
| Sodium Caseinate (SC) 3% aqueous solution | | 3 | | |
| Sodium Caseinate (SC) 1.5% aqueous solution | | | 1.5 | 1.5 |
| pH | 7 | 7 | 7 | 5 |

TABLE 2

|  | Unit (wt %) | | | | | |
| --- | --- | --- | --- | --- | --- | --- |
| Ingredients | Ex. 5 | Ex. 6 | Ex. 7 | Ex. 8 | Ex. 9 | Ex. 10 |
| Ex. 1 | 90 | 70 | 50 | 90 | 70 | 50 |
| Ex. 2 | 10 | 30 | 50 | 10 | 30 | 50 |
| pH | 7 | 7 | 7 | 5 | 5 | 5 |

HMP powder was dissolved into water under agitation to obtain 3% aqueous solution (1-3% of HMP concentration is adequate). Since the solution has a low pH, NaOH was added thereto to adjust the solution to approximately pH 7. In this manner, 3% aqueous HMP solution was prepared. In addition, SC powder was dissolved into water under agitation to obtain 3% aqueous solution (SC concentration was controlled so that it is lower than HMP concentration). After carrying out agitation sufficiently, aqueous solution of micelles was formed and the micelles had an average particle size of approximately 100-200 nm. The thus prepared solution had a pH of about 7. When the solution has an excessively high or low pH, NaOH or citric acid was used to adjust the solution to approximately pH 7. In this manner, 3% aqueous SC solution was prepared. The thus prepared 3% aqueous HMP solution was mixed with 3% aqueous SC solution at a different ratio (9:1/7:3/5:5) to obtain mixed aqueous solutions, followed by agitation.

While each mixed aqueous solution was agitated continuously at a predetermined speed, aqueous citric acid solution was added gradually thereto to lower the pH of solution to about 5. Then, the negative charges of the surface of SC micelles were converted into positive charges, which, in turn, form complexes with the negative charges of HMP. In this manner, microcapsules were formed (the surfaces of SC micelles are coated with HMP).

[Example II] Preparation of HMP/SC/Glycoprotein Capsules

While mixing the aqueous HMP solution with the aqueous SC solution in Example I, powder of green tea-derived glycoprotein (ISAI-016, Doore Co., Ltd.) was further dissolved sufficiently therein. Then, pH of the resultant solution was adjusted to obtain microcapsules to which the green tea-derived glycoprotein is introduced as an ingredient constituting the capsules.

TABLE 3

|  | Unit (wt %) |
| --- | --- |
| Ingredients | Ex. 11 |
| Green tea-derived glycoprotein | 3 |
| Water | Balance |
| pH | 7 |

TABLE 4

|  | Unit (wt %) | | | | | |
| --- | --- | --- | --- | --- | --- | --- |
| Ingredients | Ex. 12 | Ex. 13 | Ex. 14 | Ex. 15 | Ex. 16 | Ex. 17 |
| Ex. 11 | 50 | 50 | 50 | 50 | 0.1 | 0.1 |
| Ex. 1 | 50 | 50 | | | 69.969 | 69.699 |
| Ex. 2 | | | 50 | 50 | 30 | 30 |
| pH | 7 | 5 | 7 | 5 | 7 | 5 |

[Example III] Preparation of HMP/SC/Glycoprotein Capsules Having Oil in Particle Cores Aqueous o/w emulsion type solution using SC as a surfactant was used instead of the aqueous SC solution used in the above Examples. To prepare the emulsion type solution, a homomixer was used to form aqueous solution having oil drops while introducing oil to water first. Then, a predetermined amount of SC powder was introduced thereto and subjected to homomixing to obtain an o/w type emulsion solution using SC having emulsifying activity.

TABLE 5

| Ingredients | Unit (wt %) Ex. 18 |
|---|---|
| CSA(caprylic/capric triglyceride) | 20 |
| Sodium Caseinate (SC) | 3 |
| Water | Balance |

TABLE 6

| Ingredients | Unit (wt %) | | | |
|---|---|---|---|---|
| | Ex. 19 | Ex. 20 | Ex. 21 | Ex. 22 |
| Ex. 1 | 70 | 70 | 69.970 | 69.970 |
| Ex. 18 | 30 | 30 | 30 | 30 |
| Green tea-derived glycoprotein | | | 0.1 | 0.1 |
| pH | 7 | 5 | 7 | 5 |

[Example IV] Preparation of Aqueous Isolated Soy Protein (ISP) Solution

While water was agitated in an agi-mixer at room temperature under an adequate speed, isolated soy protein, Fuji Pro NT (JILIN FUJI PROTEIN Co., China), was introduced thereto to 3 wt % based on the final aqueous solution composition. While the solution was agitated continuously at room temperature, it was allowed to stand for 6 hours. The thus obtained suspension was subjected to centrifugal separation to separate the water-insoluble portion therefrom (7000 rpm, 30 minutes). Then, the precipitated water-insoluble portion was discarded and the supernatant was taken. The thus obtained aqueous ISP solution included 1.8 wt % of soy protein.

[Example V] Preparation of HMP/ISP Capsules

The following experiment was carried out according to the following composition.

TABLE 7

| Ingredients | Unit (wt %) Ex. 23 |
|---|---|
| Water | Balance |
| Isolated soy protein(ISP) | 1.8 |
| pH | 7 |

HMP powder was dissolved into water under agitation to obtain 3% aqueous solution (1-3% of HMP concentration is adequate). Since the solution had a low pH, NaOH was added thereto to adjust the solution to approximately pH 7. In this manner, 3% aqueous HMP solution was prepared. In addition, the thus prepared 3% aqueous HMP solution was mixed with the 1.8% aqueous ISP solution obtained from Example IV at a different ratio (1:1/2:1/4:1) to obtain mixed aqueous solutions, followed by agitation.

While each mixed aqueous solution was agitated continuously at a predetermined speed, aqueous citric acid solution was added gradually thereto to lower the pH of solution to about 5. Then, the negative charges on the surface of ISP nanoparticles decreased to cause a relative increase in positive charges, which, in turn, form complexes with the negative charges of HMP. In this manner, microcapsules were formed (the surfaces of ISP particles or ISP particle clusters are coated with HMP).

[Example VI] Preparation of HMP/ISP/Glycoprotein Capsules

While mixing the aqueous HMP solution with the aqueous SC solution in Example V, powder of green tea-derived glycoprotein (ISAI-016, Doore Co., Ltd.) was further dissolved therein in an amount of approximately 0.01-0.1 wt %. Then, pH of the resultant solution was adjusted (using 1M citric acid) to obtain microcapsules to which the green tea-derived glycoprotein is introduced as an ingredient constituting the capsules. In the green tea-derived glycoprotein used herein, the sugar moiety thereof includes neutral sugar (49.3 wt %)+uronic acid (50.7 wt %). (It is thought that the negative charges of uronic acid is complexed with the positive charges of the surfaces of ISP nanoparticles).

TABLE 8

| Ingredients | Unit (wt %) | | |
|---|---|---|---|
| | Ex. 24 | Ex. 25 | Ex. 26 |
| Ex. 1 | 50 | 66.9 | 80 |
| Ex. 23 | 49.9 | 33 | 19.9 |
| Green tea-derived glycoprotein | 0.1 | 0.1 | 0.1 |
| pH | 5 | 5 | 5 |

According to the following Table 9, Examples 27-30 correspond to samples prepared by adding 1M citric acid gradually to the aqueous ISP solution obtained from Example 23 under agitation and lowering pH to approximately 6, 5.5, 5 and 4.5.

TABLE 9

| Ingredients | Unit (wt %) | | | |
|---|---|---|---|---|
| | Ex. 27 | Ex. 28 | Ex. 29 | Ex. 30 |
| Water | Balance | Balance | Balance | Balance |
| ISP | 1.8 | 1.8 | 1.8 | 1.8 |
| pH | 6 | 5.5 | 5 | 4.5 |

[Example VII] Preparation of HMP/ISP/Glycoprotein Capsules or Emulsion Having Oil in Particle Cores Aqueous o/w emulsion type solution using ISP as a surfactant was used instead of the aqueous SC solution used in the above Examples. To prepare preliminary o/w emulsion, a homomixer was used while introducing a predetermined amount of oil to the aqueous ISP solution. After the primary emulsification, aqueous HMP solution (+glycoprotein) was added to obtain a mixture, and aqueous citric acid solution was added gradually thereto to lower pH to approximately 5. Then, the positive charges of the emulsion particle surfaces generated from ISP form complexes with the negative charges of HMP/glycoprotein to obtain capsules or emulsion, having oil cores emulsified preliminarily with ISP and coated with HMP. To reduce the particle size and increase the emulsion stability, a high-pressure emulsifying system is used so that the emulsion particles may have a reduced particle size.

According to the following Table 10, Examples 31-34 were obtained by using C.E.H. as ester-based oil, CSA as triglyceride-based oil, DC200 100 cs as silicone-based oil and LL14E as hydrocarbon-based oil and introducing each type of oil to Example 23, followed by homomixing (5 minutes, 7500 rpm).

TABLE 10

| Ingredients | Unit (wt %) | | | |
|---|---|---|---|---|
| | Ex. 31 | Ex. 32 | Ex. 33 | Ex. 34 |
| C.E.H | 10 | — | — | — |
| CSA | — | 10 | — | — |
| DC200 100cs | — | — | 10 | — |
| P L14E | — | — | — | 10 |
| Ex. 23 | 90 | 90 | 90 | 90 |

According to the following Table 11, Examples 35-38 were obtained by adding the aqueous HMP solution of Example 1 and green tea-derived glycoprotein to Examples 31-34 to form mixtures, carrying out homomixing (5 minutes, 5000 rpm) and lowering pH by using citric acid so that the surfaces of o/w emulsion particles emulsified preliminarily with ISP were coated with the glycoprotein and HMP by way of electrostatic bonding.

In this manner, it is possible to enhance the stability of emulsion particles using ISP. It is possible to significantly enhance the stability of o/w emulsion using ISP alone through the structural characteristics of emulsion having a multi-layer structure and the addition of negative charges to the outermost layer from HMP.

TABLE 11

| Ingredients | Unit (wt %) | | | |
|---|---|---|---|---|
| | Ex. 35 | Ex. 36 | Ex. 37 | Ex. 38 |
| Ex. 1 | 50 | 50 | 50 | 50 |
| Ex. 31 | 49.9 | — | — | — |
| Ex. 32 | — | 49.9 | — | — |
| Ex. 33 | — | — | 49.9 | — |
| Ex. 34 | — | — | — | 49.9 |
| Green tea-derived glycoprotein | 0.1 | 0.1 | 0.1 | 0.1 |
| pH | 5 | 5 | 5 | 5 |

According to the following Table 12, Examples 39-42 were prepared to observe variations in emulsion particle size in the emulsion particles obtained by using triglyceride-based oil, CSA, as oil and varying the weight ratio of oil/ISP/HMP. Since ISP is used as a preliminary emulsifier and the surfaces of the thus obtained emulsion particles are coated with HMP and green tea-derived glycoprotein, the amount of HMP was maintained in such a manner that it was higher than the amount of ISP. Examples 39-42 are prepared in the same manner as Examples 35-38.

TABLE 12

| Ingredients | Unit (wt %) | | | |
|---|---|---|---|---|
| | Ex. 39 | Ex. 40 | Ex. 41 | Ex. 42 |
| CSA | 10 | 10 | 20 | 10 |
| Ex. 23 | 49.9 | 22.4 | 19.9 | 9.9 |
| Ex. 1 | 45 | 67.5 | 60 | 80 |
| Green tea-derived glycoprotein | 0.1 | 0.1 | 0.1 | 0.1 |
| pH | 5 | 5 | 5 | 5 |

According to the following Table 13, Example 43 corresponds to a sample prepared by emulsifying 15% three type of triglyceride-based oil preliminarily with ISP in the same manner as Examples 35-38 and coating the thus preliminarily emulsified particles with HMP and glycoprotein. Example 44 is a sample obtained by further using a high-pressure emulsifying system to reduce the particle size of the resultant emulsion particles of Example 43. Herein, the high-pressure emulsifying system is Model APV 2000, which is used as soon as Example 43 was prepared for 4 cycles under 100 bars to carry out emulsification under high pressure.

TABLE 13

| Ingredients | Unit (wt %) Ex. 43 |
|---|---|
| CSA | 5 |
| Cropure MDF | 5 |
| Sunflower oil | 5 |
| Ex. 23 | 42.4 |
| Ex. 1 | 42.5 |
| Green tea-derived glycoprotein | 0.1 |
| pH | 5 |

According to the following Table 14, Examples 45-47 were prepared by varying the amount of CSA to 5%, 10% and 15% while fixing the proportions of ISP and HMP. Examples 48-50 were prepared by varying the type of triglyceride-based oil alone while fixing the oil content of 15% and the amounts of ISP and HMP. The same conditions and procedure as Examples 35-38 were used and the following composition was used herein. In addition, in Examples 45-50, a high-pressure emulsifying system was further used in the same manner as described above.

TABLE 14

| Ingredients | Unit (wt %) | | | | | |
|---|---|---|---|---|---|---|
| | Ex. 45 | Ex. 46 | Ex. 47 | Ex. 48 | Ex. 49 | Ex. 50 |
| CSA | 5 | 10 | 15 | — | — | — |
| Cropure MDF | — | — | — | 15 | — | — |
| Myritol 331 | — | — | — | — | 15 | — |
| Sunflower oil | — | — | — | — | — | 15 |
| Ex. 23 | 47.4 | 44.9 | 42.4 | 42.4 | 42.4 | 42.4 |
| Ex. 1 | 47.5 | 45 | 42.5 | 42.5 | 42.5 | 42.5 |
| Green tea-derived glycoprotein | 0.1 | 0.1 | 0.1 | 0.1 | 0.1 | 0.1 |
| pH | 5 | 5 | 5 | 5 | 5 | 5 |

[Test Example 1] Particle Size Analysis

A dynamic light scattering system (Nano-ZS available from Malvern Co.) was used to carry out particle size analysis of the 1.5% aqueous SC solution obtained from Example III and 1.8% aqueous ISP solution (pH 6.3) obtained from Example IV.

As a result, in the case of the 1.5% aqueous SC solution (FIG. 1), it was shown that it has an average particle size of 262.6 nm and PDI of 0.289, and SC forms SC micelles having the following particle size distribution in the phase of aqueous solution.

Figure 8A:
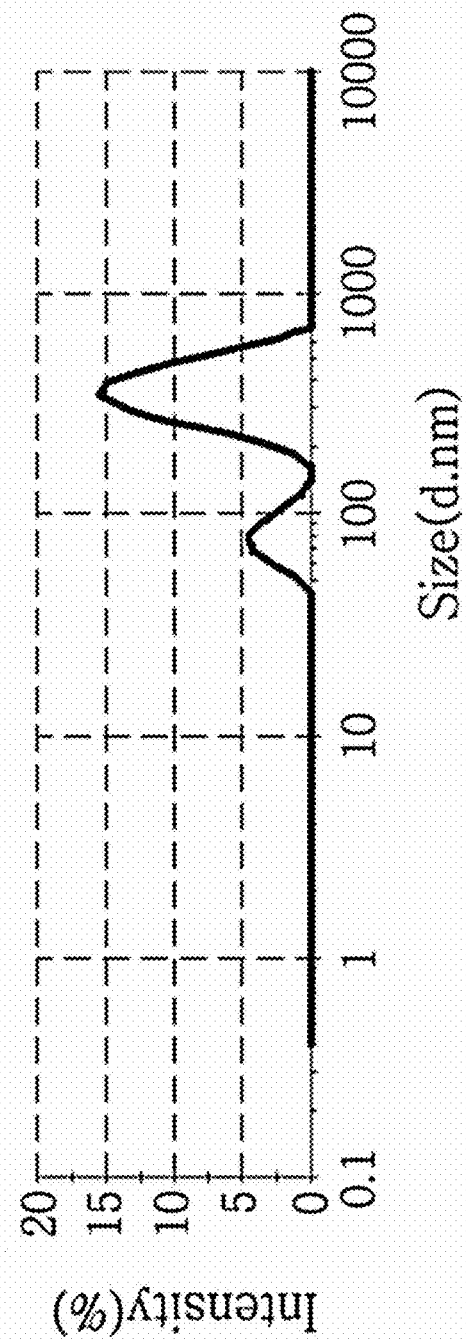
FIG. 8 is a graph showing the results of particle size analysis of ISP nanoparticles (A) and a photograph showing aqueous ISP solution (B)
Figure 8B:
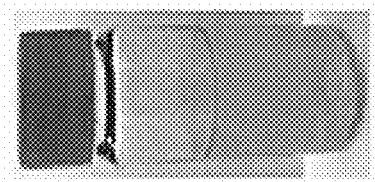

In addition, in the case of the 1.8% aqueous ISP solution (A of FIG. 8), it had an average particle size of 287 nm and PDI of 0.428, and ISP formed ISP micelles having the following particle size distribution in the phase of aqueous solution.

[Test Example 2] Surface Potential

A dynamic light scattering system (Nano-ZS available from Malvern Co.) was used to measure the surface potential of the SC micelles of the 1.5% aqueous SC solution obtained from Example III and that of the ISP micelles of the 1.8% aqueous ISP solution (pH 6.3) obtained from Example IV. An automatic titration system was used to lower pH of each sample having an initial pH of about 7 to about pH 5, and the SC micelle surface potential was determined at a specific pH.

Figure 2:
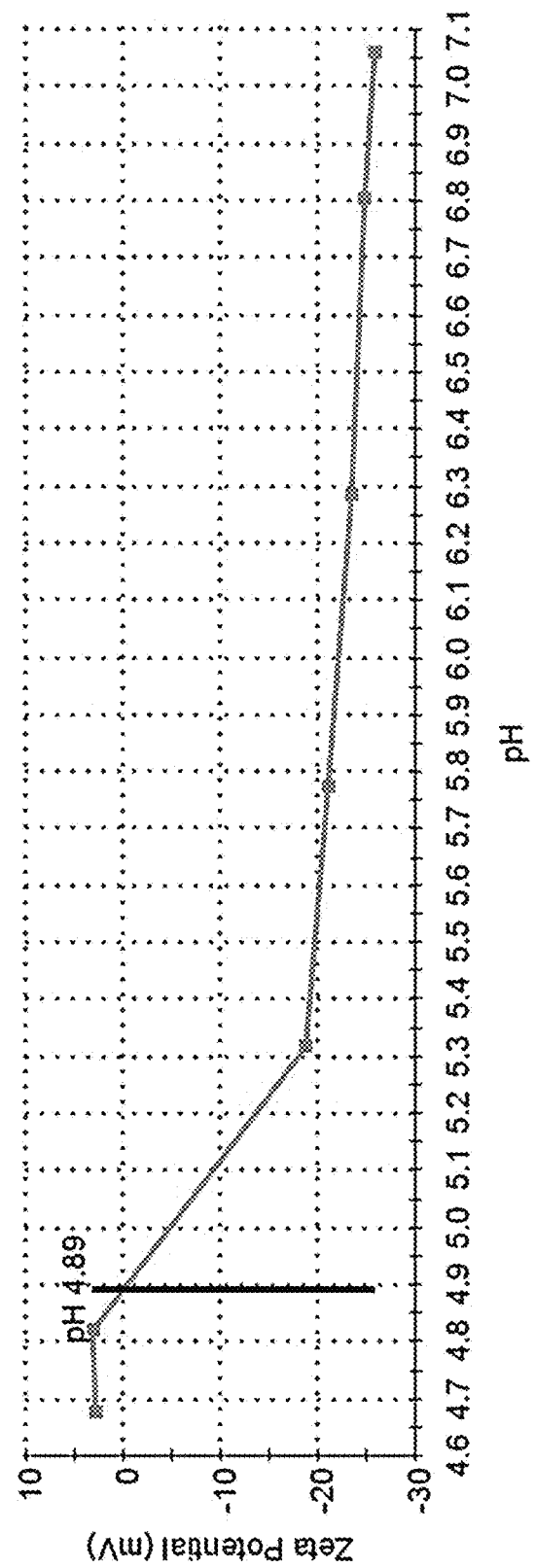
FIG. 2 is a graph showing the results of surface potential.

As a result, in the case of the SC micelle surface potential (FIG. 2), it can be seen that SC micelles having a negatively charged surface potential at high pH undergoes a change in surface potential into a positively charged surface potential approximately at an isoelectric point of 4.89, after lowering pH.

In addition, in the case of ISP micelle surface potential, the surface potential was as follows: −12.9 mV (S.D.: 3.02) at pH 7, −9.33 mV (S.D.: 2.69) at pH 6, −6.31 mV (S.D.: 4.08) at pH 5.5, −4.54 mV (S.D.: 5.64) at pH 5, and −0.86 mV (S.D.: 6.65) at pH 4.5. It can be seen that ISP micelles tend to undergo a decrease in negative charges as pH decreases similarly to SC micelles.

[Test Example 3] Turbidity and Generation of Precipitation

Figure 3:
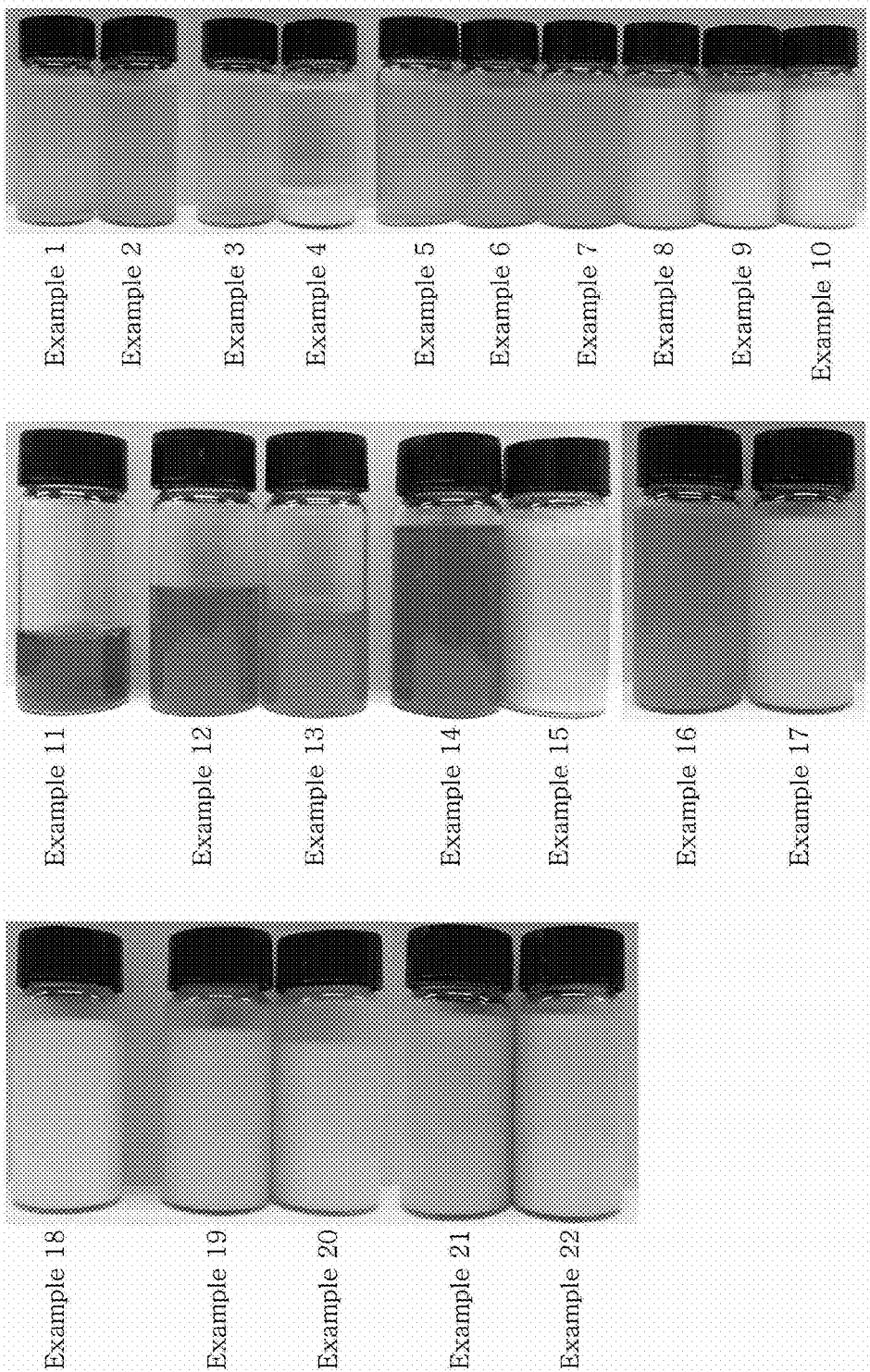
FIG. 3 is a photograph taken for the purpose of comparison of turbidity and generation of precipitation.
Figure 9:
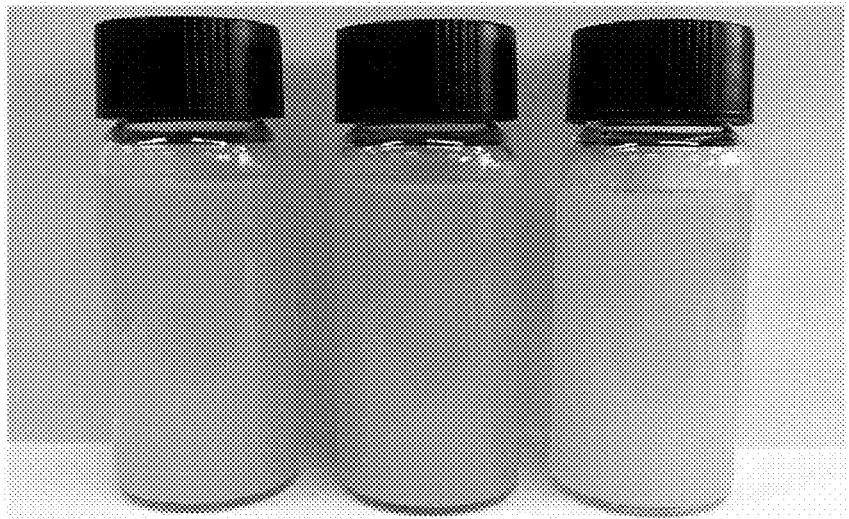
FIG. 9 shows the photographs of Examples 24-26 taken for the purpose of comparison of turbidity and generation of precipitation.
Figure 10:
FIG. 10 shows the photographs of Examples 23 and 27-30 taken for the purpose of comparison of turbidity and generation of precipitation.

To carry out comparison of turbidity and generation of precipitation among the above Examples, several photographs were taken by using a digital camera as shown in FIG. 3, FIG. 9 and FIG. 10.

Examples 1 and 2 were provided as translucent aqueous solutions. Example 3 is a translucent sample, while Example 4 causes generation of precipitation.

Examples 5-7 were provided as translucent aqueous solutions, while Examples 8-10 underwent a change in sample appearance into opaque emulsion. This is because the positive charges of HMP form complexes with the negative charges of SC micelles as pH decreases, and thus the surfaces of SC micelles are coated with HMP. Further, as the concentration ratio of HMP:SC changes from 9:1 to 5:5, a larger amount of complexes were formed to provide a high-turbidity sample.

Examples 12 and 13 caused a slight variation in color depending on pH but there was no significant change in appearance. On the contrary, it can be seen that Examples 14 and 15 undergo a change in turbidity depending on pH and causes generation of a small amount of precipitation. Therefore, it can be seen that specific complexes are formed between the green tea-derived glycoprotein and SC micelles.

In Examples 16 and 17, it can be seen that the three ingredients of HMP/SC micelles/green tea-derived glycoprotein form microcapsules having a certain particle size.

In addition, as can be seen in the photographs of Examples 18-20, the microcapsules according to the present invention have an appearance similar to the appearance of conventional emulsion, and cause no phenomena such as precipitation/separation/creaming.

It can be seen from the photographs of Examples 21 and 22 that HMP/SC/green tea-derived glycoprotein microparticles are formed with no phenomena such as precipitation/separation/creaming.

In addition, It can be seen from the photographs of Examples 24-26 (FIG. 9) that the amount of complexes decreases to provide a low-turbidity sample, as the weight ratio of HMP:ISP increases from 1:1 to 2:1 and 4:1. It can be seen from Examples 24-26 that the three ingredients of HMP/ISP nanoparticles/green tea-derived glycoprotein form microcapsules having a certain particle size.

As can be seen in the photographs of Examples 23 and 27-30 (FIG. 10), the aqueous ISP solution loses its hydrophilicity as pH decreases from 7 to 4.5 to cause precipitation. This is because while ISP originally has positive charges and negative charges, the negative charges are bound with protons due to a pH drop and lose their charges, resulting in loss of hydrophilicity. On the contrary, when mixing such aqueous ISP solution with aqueous HMP solution at a predetermined ratio and lowering pH, ISP causes no precipitation and the positive charges of ISP form ion complexes with the negative charges of HMP, thereby forming water-dispersed microparticles stably as shown in FIG. 9.

[Test Example 4] Determination of Particle Size and Uniformity

The solutions containing the microcapsules obtained from each of the above Examples are observed through an optical microscope to check whether microparticles are formed or not and to determine the structure thereof.

Figure 4:
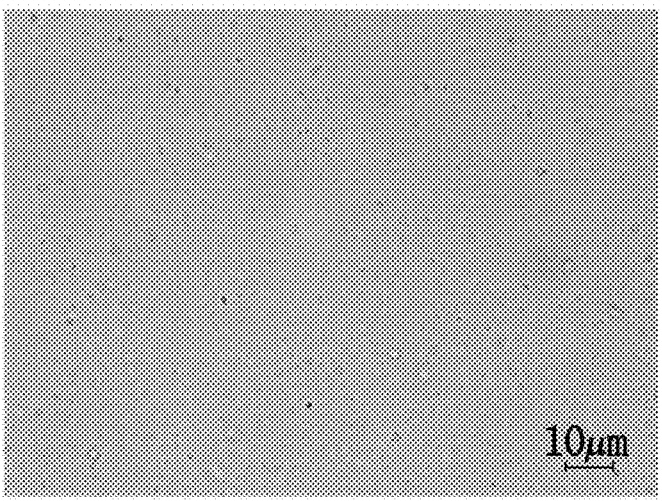
FIG. 4 to FIG. 6 show the results of determination of the particle size and uniformity (each scale bar represents 10 micrometers)
Figure 4:
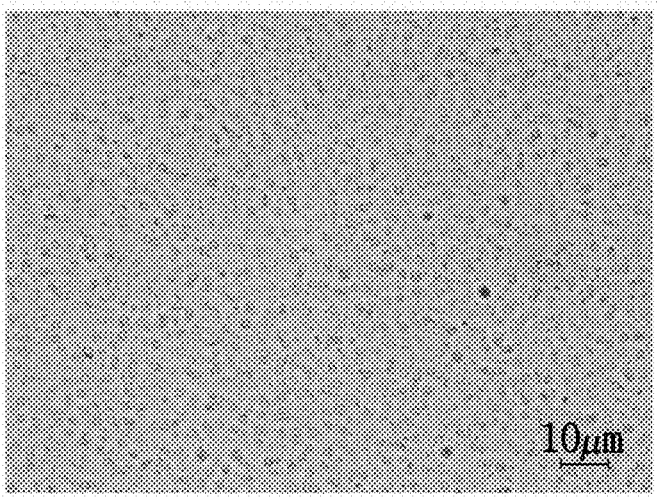
Figure 4:
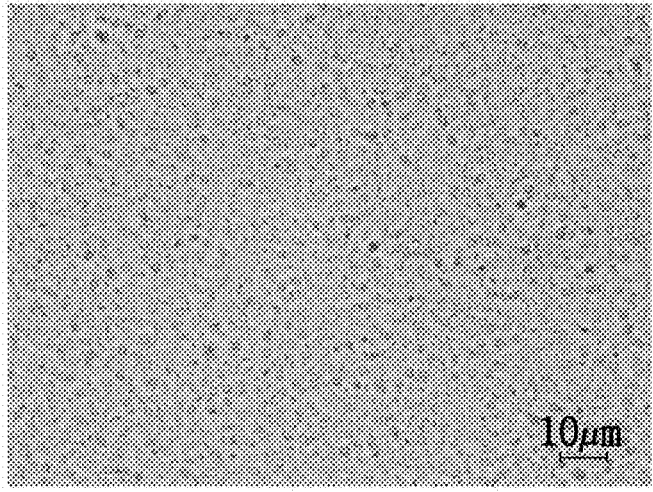

It can be seen from the optical microscopic image (FIG. 4) corresponding to Examples 8-10 that a change in ratio of HMP:SC results in a change in frequency of forming microcapsules. It can be also seen that when HMP is mixed with SC at a ratio equal to or higher than 7:3 and pH is controlled, stable microcapsules (SC micelles coated with HMP) having a relatively uniform particle size are formed.

Figure 5:
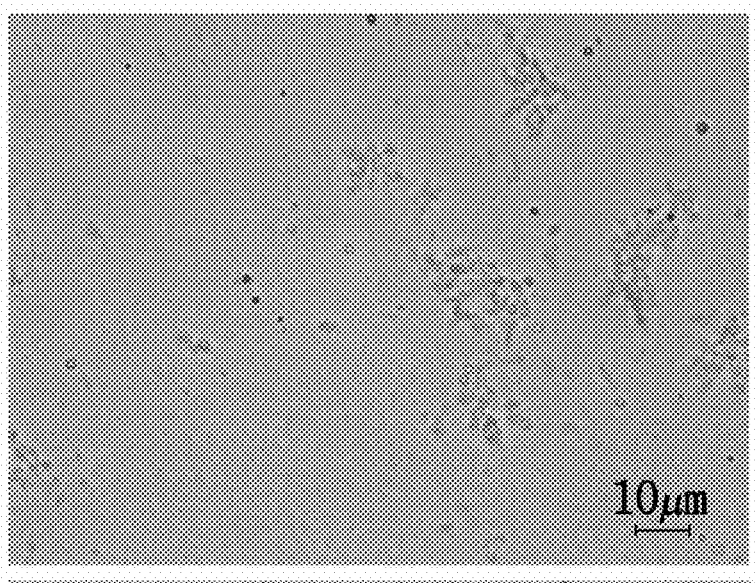
Figure 5:
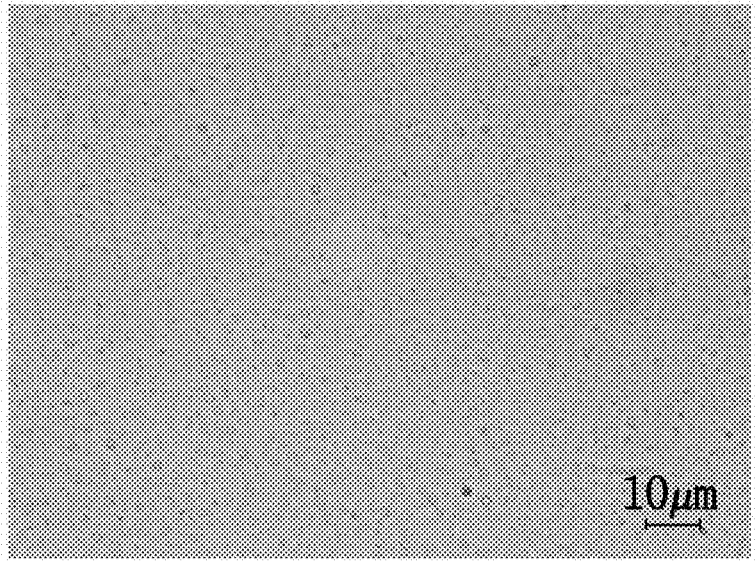

In addition, as can be seen from the optical microscopic image (FIG. 5) corresponding to Example 15, the particles appearing in the optical images of mixtures of HMP with SC are also shown partially in the images of mixtures of green tea-derived glycoprotein with SC. This indirectly suggests that the surfaces of SC micelles are coated partially with green tea-derived glycoprotein through ion bonding. However, it is difficult to observe particles having a uniform particle size distribution of homogeneous spherical particles like the microcapsules obtained by complexing between HMP and SC. On the contrary, as can be seen from the optical microscopic image (FIG. 5) corresponding to Example 17, the microcapsules obtained by the combination of HMP/SC/green tea-derived glycoprotein are provided as spherical microcapsules having a very uniform particle size distribution. Therefore, it can be seen that SC micelles are coated uniformly with green tea-derived glycoprotein and HMP through ion bonding to form capsules.

Figure 6:
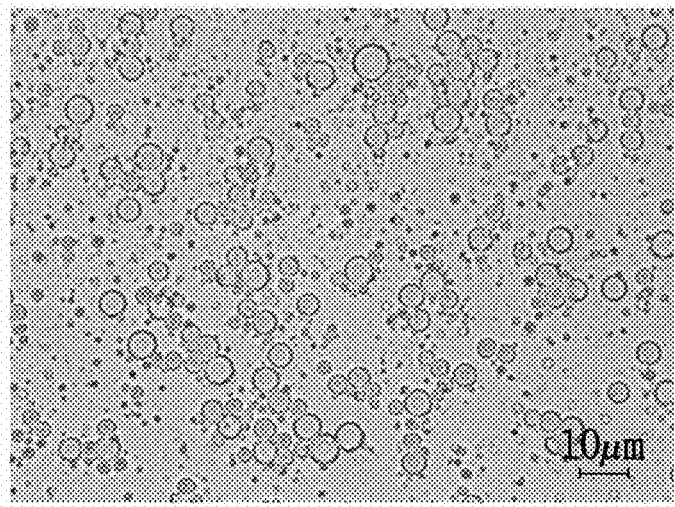
Figure 6:
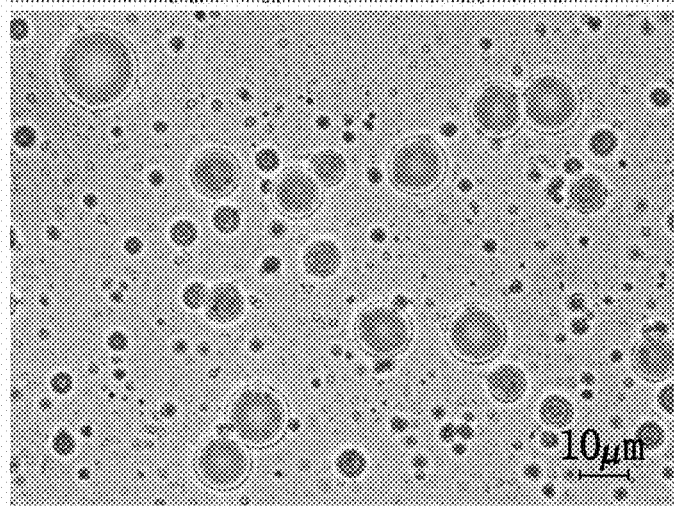
Figure 6:
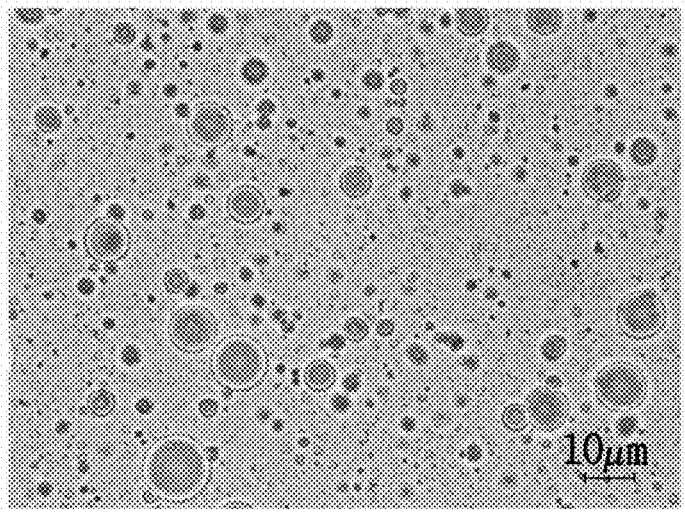

Further, as shown in the optical microscopic image (FIG. 6) of Example 18, the emulsion particles have a particle size of about several micrometers-10 micrometers due to SC, and are provided as o/w emulsion. As shown in the optical microscopic image (FIG. 6) of Example 20, the particles have a slightly increased particle size as compared to Example 18, and a multi-layer structure regarded as a HMP coating layer is formed.

In addition, it can be seen from the optical microscopic image (FIG. 6) corresponding to Example 22 that microcapsules of HMP/SC/green tea-derived glycoprotein having CSA in their cores are formed.

Particularly, it can be seen that when viewed from the cores of the capsules according to Examples 20 and 22, the capsules have a multi-layer structure of CSA (oil), SC micelles, HMP (+green tea-derived glycoprotein).

Figure 11:
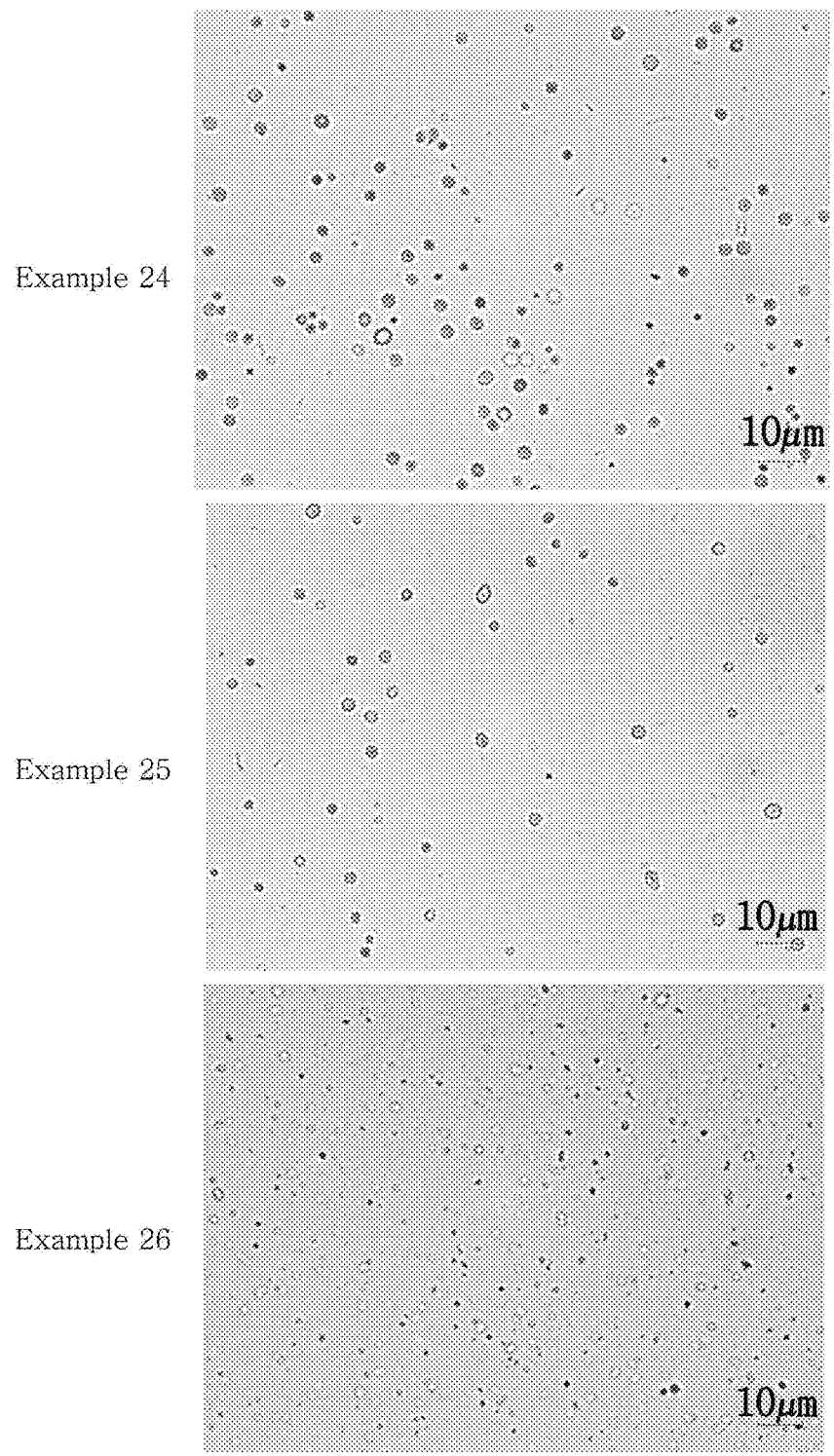
FIG. 11 to FIG. 15 show the results of determination of the particle size and uniformity of Examples 24-26 and 35-50 (each scale bar represents 10 micrometers.

As shown in the optical microscopic images (FIG. 11) of Examples 24-26, depending on the mixing ratio of aqueous HMP solution with aqueous ISP solution, the resultant ion complex microcapsules have a variable particle size. From Example 24 to Example 26, the amount of ISP forming the core portions of capsules decreases, resulting in a decrease in particle size of microcapsules observed by the microscopic images. Therefore, it can be seen that a higher amount of ISP provides particles having a larger particle size and a lower amount of ISP provides particles having a smaller particle size. In addition, it can be also seen from the optical microscopic images that when the negative charges of ISP particles are bound with the protons and lose their hydrophilicity, the presence of HMP allows ion bonding between the negative charges of HMP and the positive charges of ISP so that ISP may be coated, and thus the resultant capsules are dispersed in water in the form of spherical particles.

Figure 12:
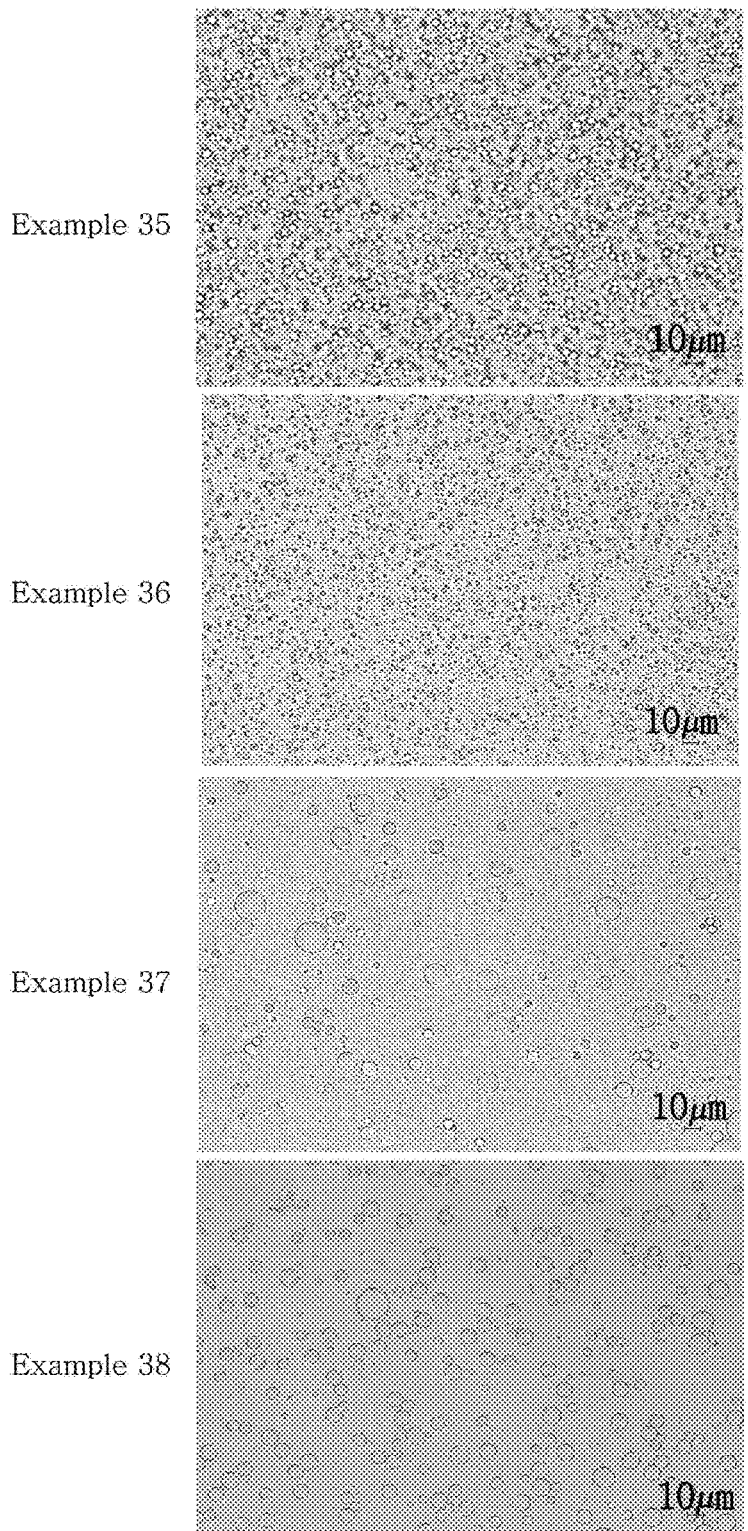

As shown in the optical microscopic images of Examples 35-38 (FIG. 12), the emulsion particles of Examples 35 and 36 using triglyceride-based oil or ester-based oil are significantly smaller than the emulsion particles of Examples 37 and 38 using silicone-based oil or hydrocarbon-based oil. Therefore, it is thought that smaller emulsion particles increase the overall stability of an emulsion system, and thus preparation of emulsion particles (microcapsules) and emulsion including the same using triglyceride oil-based or ester-based oil are preferred in terms of emulsion stability.

Figure 13:
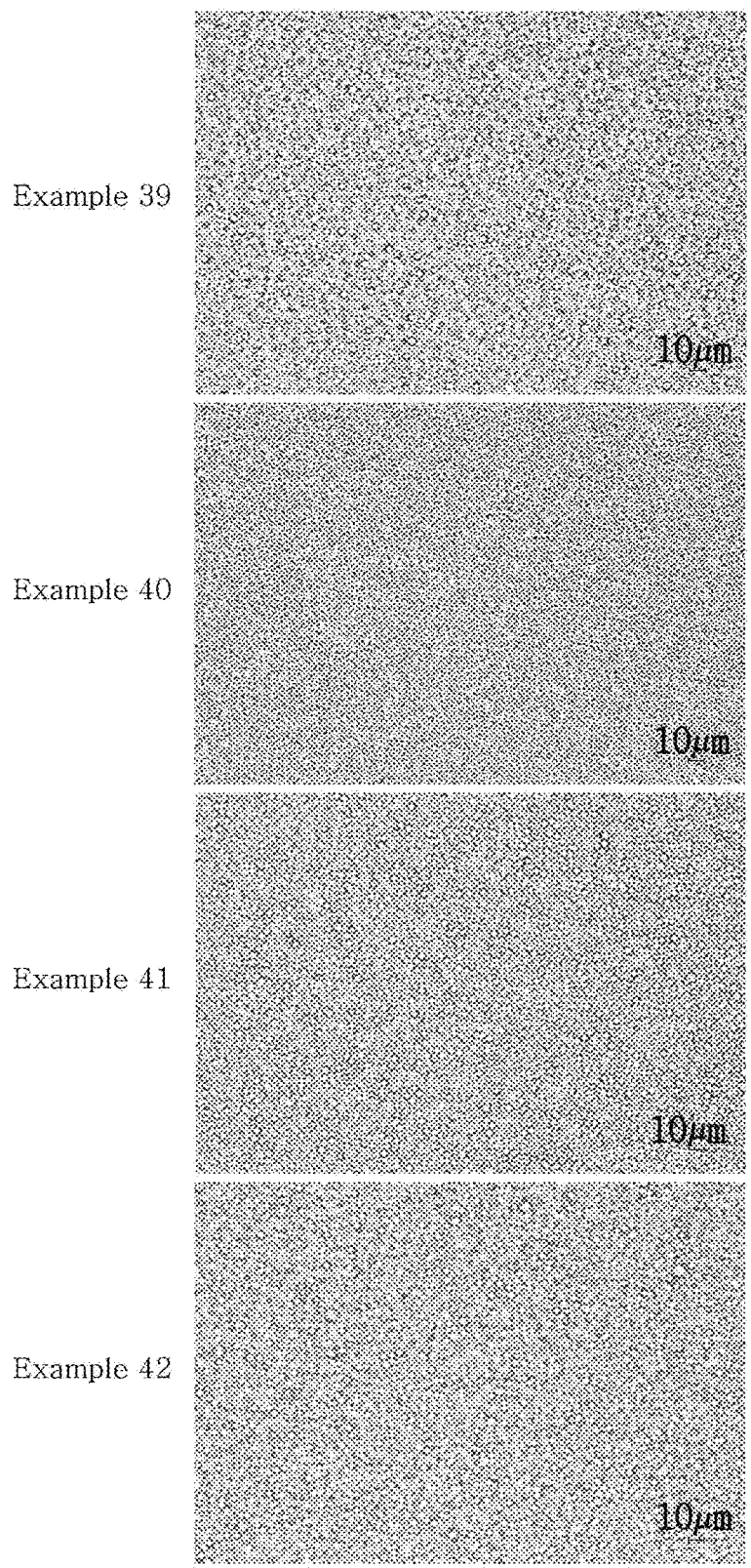

As shown in the optical microscopic images of Examples 39-42 (FIG. 13), the emulsion particles or emulsion of Example 40 have the smallest particle size and show the most preferred emulsion stability. The tests of Examples 39-42 cover an ISP content of about 0.178%-0.81% based on the finished contents, while the HMP content ranges from about 1.35% to 2.4%. It is thought that sufficiently stable emulsion particles may be obtained even when the content of ISP or HMP is higher or lower than the above-defined ranges. However, it is expected that more stable emulsion particles may be obtained as the amount of ISP/HMP increases. However, considering the finished product and formulation used therefor, it is not preferred to increase the amount thoughtlessly. Therefore, in the case of a formulation, such as emulsion, it is thought that an oil content of about 0-30 wt %, ISP content of 0.1-1 wt % and HMP content of about 1-3 wt % based on the total weight of the finished product or formulation are preferred.

Figure 14:
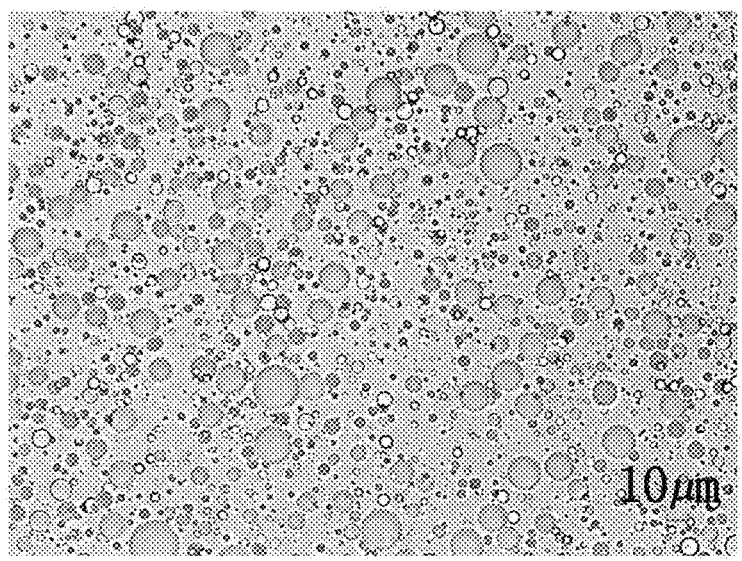
Figure 14:
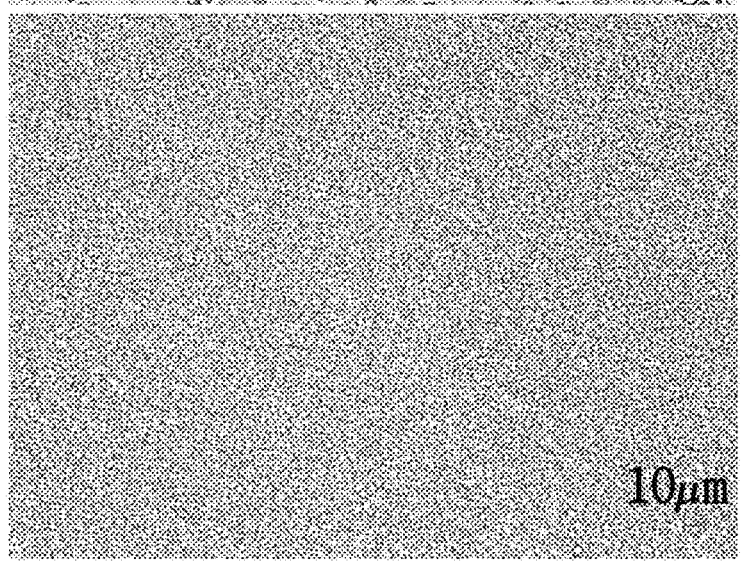

As shown in the optical microscopic images of Examples 43 and 44 (FIG. 14), Example 44 using a high-pressure emulsifying system provides a significantly smaller emulsion particle size as compared to Example 43 using no high-pressure emulsifying system. This demonstrates that high-pressure emulsification increases the stability of a finished emulsion. In addition, Example 44 provides suspended emulsion contents having a low viscosity (<100 cps), which, otherwise, are not obtained by using a conventional emulsifier with ease.

Figure 15:
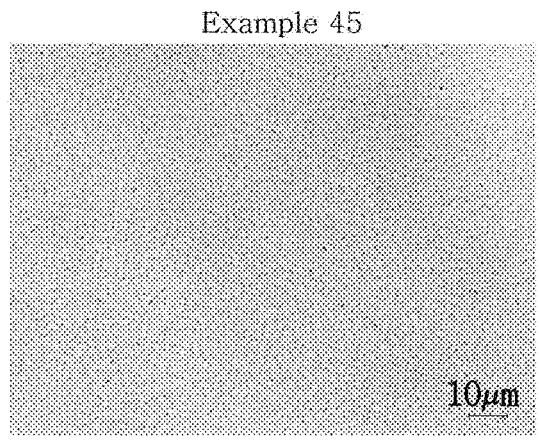
Figure 15:
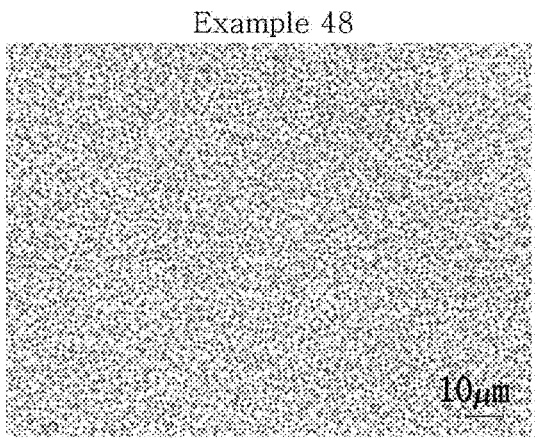
Figure 15:
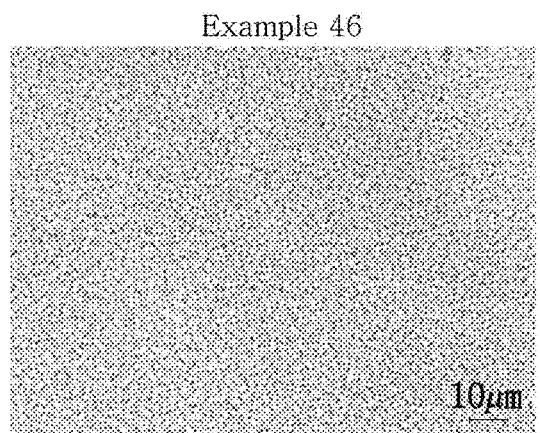
Figure 15:
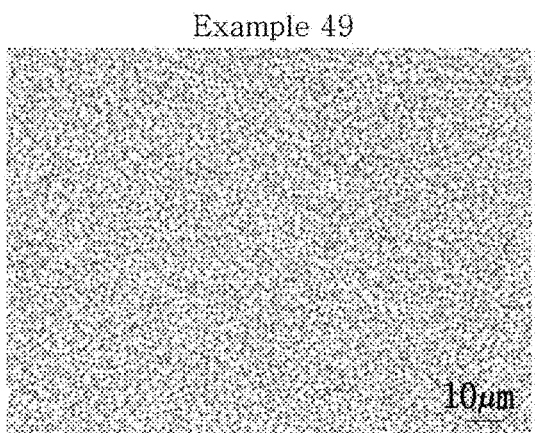
Figure 15:
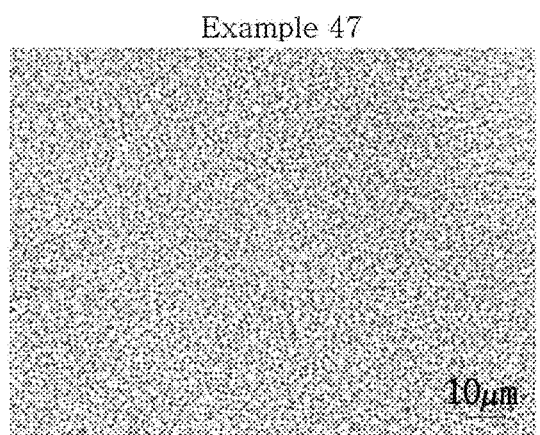
Figure 15:
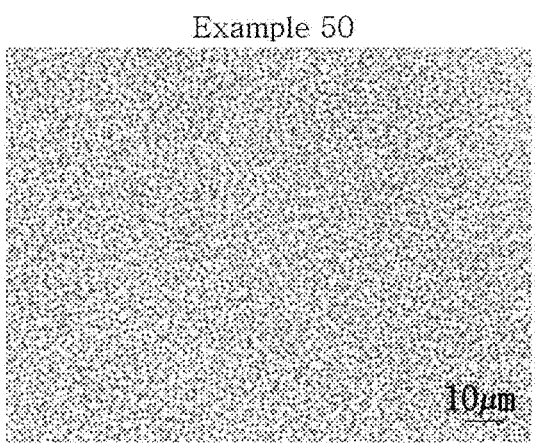

As shown in the optical microscopic images of Examples 45-50 (FIG. 15), as the oil phase content of o/w emulsion in Examples 45-47 increases from 5% to 15%, the emulsion particles have a slightly increased particle size. In addition, it can be seen from Examples 48-50 that when an oil content is maintained at about 15% even though the particular type of oil is changed in the same class, there is no significant effect upon the size of emulsion particles.

[Test Example 5] Determination of Anti-Oxidative Activity

To evaluate anti-oxidative activity, DPPH (1,1-diphenyl-2-picrylhydrazyl) assay was carried out. The samples used in this test (Doore Co., Ltd.) are as follows.

TABLE 15

| Sample code | Sample name |
|---|---|
| ISAI-016 | Green tea-derived glycoprotein |
| ISAI-017 | Ginseng-derived glycoprotein |
| ISAI-018 | Pine tree leave-derived glycoprotein |
| ISAI-019 | *Abies*-derived glycoprotein |
| ISAI-020 | *Rhodiola*-derived glycoprotein |
| ISAI-021 | *Bergenia*-derived glycoprotein |

DPPH assay is a test in which an oxidant called DPPH is used to initiate oxidation and the ability of a sample to be tested in removing radicals is determined. When DPPH meets a material having anti-oxidative activity, it donates electrons to cause radical removing and undergoes a change in color from purple to yellow. Thus, it is possible to observe the oxidative activity of a material easily with the naked eye.

Each sample was introduced to a 96-well plate in an amount of 10 μl, and 100 μM of DPPH was introduced thereto in an amount of 190 μl. After carrying out reaction at 37° C. for 30 minutes, the absorbance was measured at 517 nm. Vitamin C was used as positive control (10, 5, 2.5 μg/ml).

Figure 7:
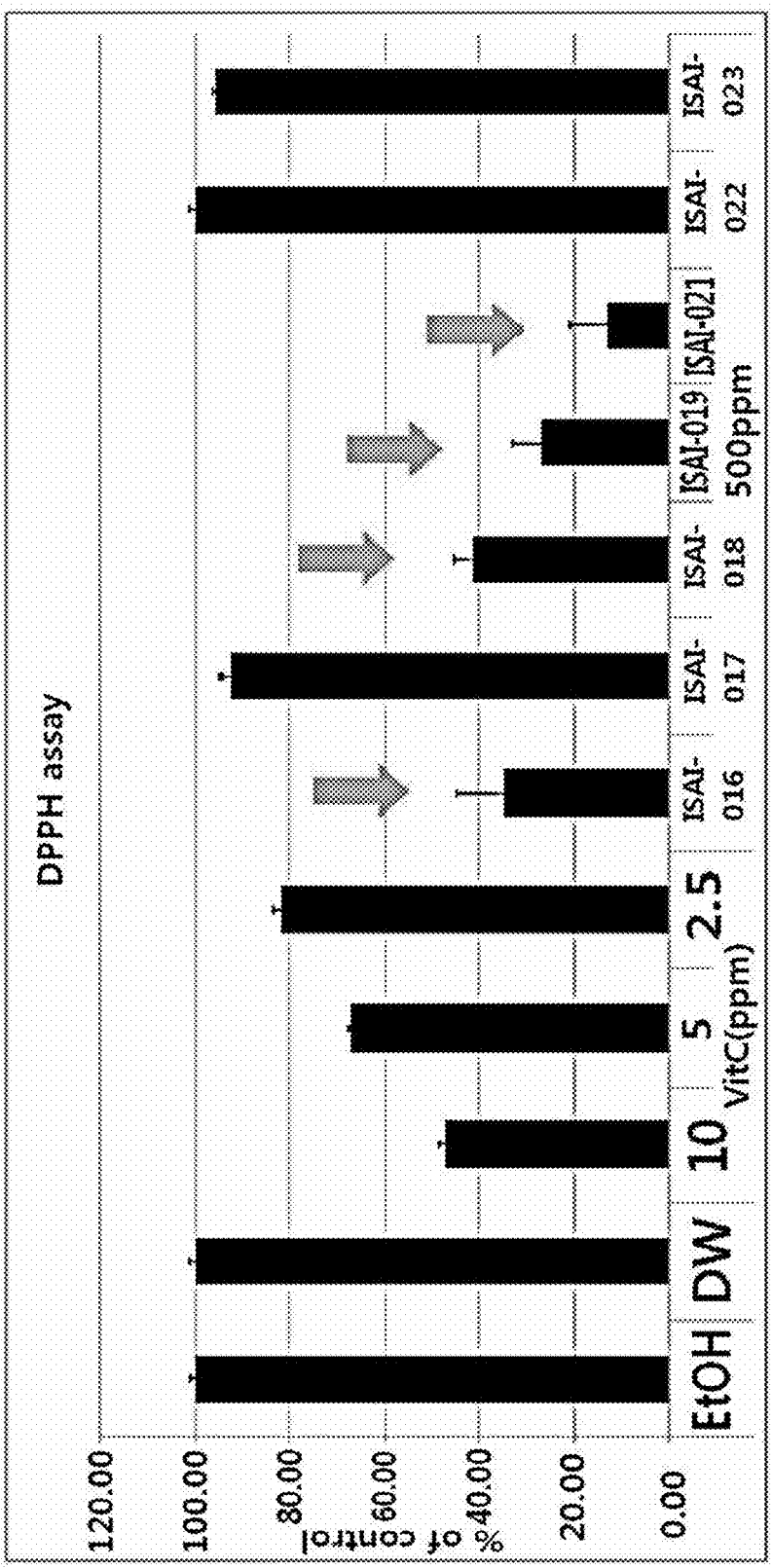
FIG. 7 is a graph showing the results of the anti-oxidative activity of a plant-derived glycoprotein.

As a result (FIG. 7), it is shown that high anti-oxidative activity is provided in the order of *bergenia*-derived glycoprotein (ISAI-021)>green tea-derived glycoprotein (ISAI-016)=*abies*-derived glycoprotein (ISAI-019)>pine tree leave-derived glycoprotein (ISAI-018).

Since both the main ingredients of capsules, i.e., sodium caseinate (ISAI-022) and pectin (ISAI-023) have no radical scavenging activity, introduction of the above-mentioned glycoproteins enhances anti-oxidative activity and improves the effect of a carrier.

[Test Example 6] Determination of Stability of Internal Ingredients of Oil Cores One type of cosmetic active ingredients, coenzyme-Q10, was stabilized in the HMP/SC/green tea-derived glycoprotein multi-layer microcapsules having oil cores obtained as described above, and compared with the stabilization effect of coenzyme-Q10 stabilized in a conventional o/w formulation in terms of stabilization effect.

First, the following Example 52 was used to prepare HMP/SC/green tea-derived glycoprotein microcapsules having oil cores.

TABLE 16

| | Unit (wt %) | |
|---|---|---|
| Ingredients | Ex. 51 | Ex. 52 |
| Coenzyme-Q10 | 2 | |
| CSA | 20 | |
| Ex. 1 | | 49.9 |
| Ex. 51 | | 50 |
| SC | 3 | |
| Green tea-derived glycoprotein | | 0.1 |
| pH | 7 | 5 |
| Water | Balance | Balance |

First, 10% of coenzyme-Q10 (Q10) was dissolved into CSA, and 20% of 10% Q10-containing oil was emulsified with 3% of SC in the same manner as described in Example 18 to obtain Example 51. The thus obtained Q10/CSA/SC emulsion (Example 51) was mixed with the 3% aqueous HMP solution of Example 1 at a ratio of 1:1, and 0.1% of green tea-derived glycoprotein was dissolved further therein. While the solution is agitated sufficiently, 1M citric acid was added gradually thereto to adjust pH from about 7 to about 5. In this manner, provided were HMP/SC/green tea-derived glycoprotein microcapsules having CSA oil containing Q10 dissolved therein in their cores.

In addition, as Comparative Example 1, 1% Q10 stabilized in a conventional o/w emulsion was prepared as control of the microcapsules in which 1% of Q10 was stabilized as mentioned above (Example 52). Comparative Example 1 has the following composition.

TABLE 17

| Ingredients | Unit (wt %) Comp. Ex. 1 |
|---|---|
| Coenzyme Q10 | 1 |
| EDTA-2Na | 0.02 |
| Glycerin | 5 |
| Vegetable cured oil | 1.5 |
| Stearic acid | 0.6 |
| Glyceryl stearate | 1 |
| Cetearyl alcohol | 2 |
| Arachidyl/behenyl alcohol & Arachidyl glucoside | 1 |
| Cetearyl alcohol & Cetearyl glucoside | 2 |
| Liquid paraffin | 6 |
| Caprylic/capric triglyceride | 6 |
| Carbomer | 0.05 |
| Triethanolamine | 0.05 |
| Preservative, fragrance, colorant | q.s. ad |
| Purified water | Balance |

After determining the Q10 stabilities of the samples corresponding to Example 52 and Comparative Example 1 at room temperature and 40° C. for 4 weeks, the following results of stabilities were obtained for initial 4 weeks as compared to the initial Q10 content. Through the following results, it is shown that the Q10 stability of the microcapsulated sample is superior than Comparative Example.

TABLE 18

| | | Q10 titer (vs. initial value, %) | | |
|---|---|---|---|---|
| | | Initial | 2 weeks | 4 weeks |
| Ex. 52 | Room temperature | 100 | 100 | 100 |
| | 40° C. | | 100 | 100 |
| Comp. Ex. 1 | Room temperature | 100 | 88.2 | 82.9 |
| | 40° C. | | 88.7 | 80.6 |

[Test Example 7] Evaluation for Skin Safety

To determine the skin safety of each sample according to the inventive examples, 18 female adults and 12 male adults (average age: 32.5) were allowed to participate in a test including applying a patch of each sample. In this manner, the skin safety of the composition according to the present invention was evaluated.

Particularly, each sample patch was applied and then removed after the lapse of 28 hours. After 30 minutes, the first reading was carried out. Then, the second reading was carried out after the lapse of 96 hours. To check the intensity of skin irritation caused by each sample, weighted values were imparted depending on degrees of the positive reaction of the skin to calculate average skin reactivity. In this manner, skin irritation caused by each sample was evaluated with the naked eye. The results are shown in the following Table.

TABLE 19

| Test substance | Average reactivity | Judged grade |
|---|---|---|
| Ex. 8 | 0 | No irritation |
| Ex. 9 | 0 | No irritation |
| Ex. 10 | 0 | No irritation |
| Ex. 17 | 0 | No irritation |
| Ex. 20 | 0 | No irritation |
| Ex. 22 | 0 | No irritation |
| Ex. 52 | 0 | No irritation |
| Comp. Ex. 1 | 0 | No irritation |
| Ex. 35 | 0 | No irritation |
| Ex. 36 | 0 | No irritation |
| Ex. 37 | 0 | No irritation |
| Ex. 38 | 0 | No irritation |
| Ex. 39 | 0 | No irritation |
| Ex. 40 | 0 | No irritation |
| Ex. 41 | 0 | No irritation |
| Ex. 42 | 0 | No irritation |
| Ex. 43 | 0 | No irritation |
| Ex. 44 | 0 | No irritation |
| Ex. 45 | 0 | No irritation |
| Ex. 46 | 0 | No irritation |
| Ex. 47 | 0 | No irritation |
| Ex. 48 | 0 | No irritation |
| Ex. 49 | 0 | No irritation |
| Ex. 50 | 0 | No irritation |

As shown in Table 19, it can be seen that all of Examples 8, 9, 10, 17. 20, 22, 52, Comparative Example 1 and Examples 35-50 cause no skin irritation.

Therefore, it is demonstrated that the cosmetic composition according to the present invention has excellent skin safety.

While the exemplary embodiments have been shown and described, it will be understood by those skilled in the art that various changes in form and details may be made thereto without departing from the scope of this disclosure as defined by the appended claims. Therefore, it is intended that the scope of the present invention includes all embodiments falling within the spirit and scope of the appended claims.

The invention claimed is:

1. Microcapsules having a multi-layer structure comprising a core comprising a fat-soluble material, wherein the microcapsules further comprise
   a polysaccharide having a negative net charge;
   a protein having a isoelectric point (PI) of 4-6; and
   a plant-derived glycoprotein having a negative net charge and anti-oxidative activity,
   wherein the plant-derived glycoprotein is at least one selected from the group consisting of *bergenia*-derived glycoprotein, green tea-derived glycoprotein, *ginseng*-derived glycoprotein, pine tree leave-derived glycoprotein, and *abies*-derived glycoprotein,
   wherein a weight ratio of the polysaccharide, the protein, and the glycoprotein is 9-1:1:0.01-0.99, and
   wherein the microcapsules have the multi-layer structure comprising the core; the protein; the polysaccharide and the plant-derived glycoprotein, when viewed from the core.

2. The microcapsules according to claim 1, wherein the plant-derived glycoprotein has a carboxylic acid functional group.

3. The microcapsules according to claim 1, wherein the polysaccharide is at least one selected from the group consisting of pectin, carrageenan, gum arabic, inulin, methyl cellulose, xanthan gum, flaxseed gum, gellan gum, dextran sulfate, galactomannans, and alginate.

4. The microcapsules according to claim 1, wherein the protein is at least one selected from the group consisting of soy protein, casein, ovalbumin and lactoglobulin.

5. The microcapsules according to claim 4, wherein the soy protein is soybean protein.

6. The microcapsules according to claim 1, wherein the fat-soluble material is one that is soluble in ester-based oil, triglyceride-based oil, silicone-based oil or hydrocarbon-based oil.

7. A method for preparing the microcapsule according to claim 1, comprising the steps of:
  i) preliminarily emulsifying the fat-soluble material with the protein having an isoelectric point (PI) of 4-6 to form a preliminary o/w emulsion; and
  ii) secondary emulsifying formed preliminary emulsion with the polysaccharide having a negative net charge and the plant-derived glycoprotein having a negative net charge,
  wherein steps i) and ii) are carried out under pH 6-7, and the method further comprises step iii) reducing pH of the secondary emulsified emulsion to pH 4.8-5.2, thereby forming microcapsules.

8. An emulsion composition comprising the microcapsules as defined in claim 1.

9. The emulsion composition according to claim 8, wherein the protein is present in an amount of 0.1-1 wt % based on the total weight of the emulsion composition comprising microcapsules.

10. The emulsion composition according to claim 8, wherein the polysaccharide is present in an amount of 1-3 wt % based on the total weight of the emulsion composition comprising microcapsules.

11. The emulsion composition according to claim 8, wherein the fat-soluble material is present in an amount of 0.01-30 wt % based on the total weight of the emulsion composition comprising microcapsules.

12. The microcapsules according to claim 3, wherein the pectin is beet pectin, and the carrageenan is at least one selected from the group consisting of κ-carrageenan and ι-carrageenan.

* * * * *